United States Patent [19]

Longhurst

[11] Patent Number: 4,992,471
[45] Date of Patent: Feb. 12, 1991

[54] MOLLUSCICIDES

[75] Inventor: Christopher Longhurst, Hants, England

[73] Assignee: Lilly Industries Limited, Basingstoke, United Kingdom

[21] Appl. No.: 27,597

[22] Filed: Mar. 18, 1987

[30] Foreign Application Priority Data

Mar. 21, 1986 [GB] United Kingdom ................ 8607033

[51] Int. Cl.$^5$ ...................... A01N 37/18; A01N 37/34
[52] U.S. Cl. .................................. 514/613; 514/522; 514/628; 424/84
[58] Field of Search ........................ 514/628, 613, 522; 424/84

[56] References Cited

FOREIGN PATENT DOCUMENTS 1546820 10/1967 France .
1255161 12/1971 United Kingdom .

OTHER PUBLICATIONS

Derwent G3104, Abstract of Russian Patent No. 166,198, 6/85.
Derwent H6698, Abstract of Russian Patent No. 218,562, 1968.
Derwent H7671, Abstract of German Patent No. 1768041, 9/29/69.
Byul. Vses. Inst. Gelimintol. im, Skrayabina 1971 (5): 15–19, Application of Carboxylic Acid Amides to Control Ground Mollusks, V. V. Gorokhov and N. A. Aliev (and translation).
Byul. Vses. Inst. Gelmintol, im. Skryabina, No. 9, 1972, pp. 31–36, Comparative Test of Molluskocidal Efficacy of Various Application Forms of Metaldehyde and Preparation No. 19 in Field Conditions, V. V. Gorokhov and A. I. Krylov (and translation).
Derwent H4948, Abstract of French Patent No. 1,546,820, 11/22/68.

Primary Examiner—Allen J. Robinson
Attorney, Agent, or Firm—Kathleen R. S. Page; Leroy Whitaker

[57] ABSTRACT

A method and composition for controlling molluscs employs fluorinated carboxanilides.

5 Claims, No Drawings

MOLLUSCICIDES

This invention relates to molluscicides.

Molluscs, such as slugs and snails, are serious pests in agriculture and horticulture. They can cause great damage to crops and other cultivated plants, and much effort has been made in attempts to combat these pests with improved molluscicides. As well as terrestrial molluscs, aquatic molluscs, such as the water snails, can cause great damage, and additionally may constitute a health hazard, being hosts to parasites which carry diseases such as bilharzia.

There is, therefore, a continuing need for improved methods of controlling these pests for both economic and health reasons.

This invention provides a method of controlling molluscs which comprises applying to the locus of the molluscs as effective amount of a compound of formula

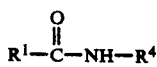
(I)

wherein $R^1$ represents an optionally monsubstituted perfluorocyclohexyl group of formula $-C_6F_{10}R^2$, a group $-C_3F_7$ or a group $-CF(CF_3)R^3$, wherein $R^2$ represents fluoro, chloro, $-CF_3$ or $-OCF_3$ and $R^3$ represents $-OC_2F_5$, $-OC_3H_7$ or perfluoromorpholino;

$R^4$ represents 5-nitro-2-pyridyl or a substituted aryl group of the formula

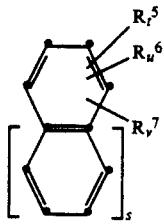

wherein:
each $R^5$ independently represents bromo or chloro;
each $R^6$ independently represents iodo, nitro, cyano, $CF_3$ or fluorosulfonyl;
$R^7$ represents methyl;
t represents 0–5;
u represents 0–2;
v represents 0, or, when at least one $R^5$ or nitro group is present, 1;
s represents 0 or 1;
and the sum of t, u and v is 2–5 when each of u, v and s is 0 or 2–3 when any of u, v and s is at least one;
or a sodium, potassium or ammonium salt of the foregoing compound, wherein ammonium is of the following formula

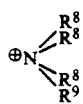

wherein each $R^8$ independently represents alkyl of $C_1$–$C_{20}$, benzyl, 2-hydroxyethyl, 2-hydroxypropyl, or 3-hydroxypropyl; and $R^9$ represents hydrogen or $R^8$, the total number of carbon atoms in all $R^8$ and $R^9$ moieties being from 12 to 60, except that when one or more $R^8$ groups are 2-hydroxyethyl, 2-hydroxypropyl, or 3-hydroxypropyl, the total number of carbon atoms in all $R^8$ and $R^9$ moieties can be from 6 to 60.

By the term $C_3F_7$ above is meant a straight or branched chain perfluoropropyl group, and includes n-$C_3F_7$ and iso-$C_3F_7$.

Also provided by the invention is a composition for use as a molluscicide which comprises a compound of formula I together with a suitable diluent or carrier therefor.

The invention may be used in controlling terrestrial or aquatic molluscs.

The preferred compounds are those wherein u is 2, t is 0, v is 0 and one of the $R^6$ groups is nitro and the other is iodo or $CF_3$ or t is 1, u is 1, $R^5$ is bromo or chloro and $R^6$ is nitro, and those wherein $R^4$ is undecafluorohexanyl, $-C_3F_7$ or $-CF(CF_3)R^3$ wherein $R^3$ is perfluoromorpholino.

Particularly preferred are the following compounds:
2'-Bromo-4'-nitro-1,2,2,3,3,4,4,5,5,6,6-undecafluorocyclohexanecarboxanilide
2'-Chloro-4'-nitro-1,2,2,3,3,4,4,5,5,6,6-undecafluorocyclohexanecarboxanilide
2'-Iodo-4'-nitro-1,2,2,3,3,4,4,5,5,6,6-undecafluorocyclohexanecarboxanilide
2'-(trifluoromethyl)-4'-nitro-2,3,3,3-tetrafluoro-2-(trifluoromethyl)propionanilide
2',5'-Dichloro-4'-nitro-2,3,3,3-tetrafluoro-2-(trifluoromethyl)propionanilide
2'-Bromo-4'-nitro-2,3,3,3-tetrafluoro-2-(octafluoromorpholino)propionanilide.

When used against terrestrial molluscs, the composition will preferably take the form of a bait containing, for example, bait materials, fillers and optionally waterproofing agents, while for use against aquatic molluscs the composition will preferably take the form of a paint, gel or slow-release polymer or granule.

The method of the invention may also be carried out by spraying diluted concentrates as water dispersions or emulsions, which may be sprayed onto the molluscs, their locations or food sources. The concentrates may take the form of solid concentrates, such as wettable powders or dry flowable powders, or liquid emulsifiable concentrates or aqueous suspensions. The compounds may also be applied to mollusc loci as dusts or granules.

The compounds useful in the present invention are prepared by conventional procedures for the synthesis of carboxanilides. However, a preferred method of synthesis of those compounds wherein RI is a fluorinated cyclohexyl group is the reaction of an acyl halide and an aniline, 1-aminonaphthalene, or 2-amino-5-nitropyridine, in accordance with the following scheme:

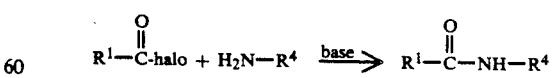

and although other conventional methods are believed to be available, no advantage over the foregoing method is expected.

The acyl halide is preferably an acyl fluoride. The acyl fluorides are obtained directly in the electrochemical fluorination process by which the fluorinated cycloalkyl ($R^1$) group is achieved, and thus require no additional reaction prior to their use in preparing the compounds of the present invention.

A preferred method for the remaining compounds is the reaction of the appropriate alkanoyl halide with the desired aniline, 1-aminonaphthalene, or 2-amino-5-nitropyridine, of the formula

H$_2$N—R$^4$

Preferably the halide is fluoride.

In carrying out these reactions, the reactants are combined in a reaction solvent. Various solvents can be employed, including toluene, acetonitrile, diethyl ether, tetrahydrofuran, and halogenated solvents such as methylene chloride. In general, diethyl ether and halogenated solvents are preferred A halogenated solvent can sometimes serve as the solvent in a "one-pot" reaction to make the aniline starting material which is thereafter converted to the final product of the invention. In other particulars, the reaction is conventional. An HF acceptor is provided to the reaction mixture; typically triethylamine is used. The reaction consumes the reactants and the HF acceptor in equimolar amounts. The reaction goes forward over a wide temperature range, such as from 10° to 110° C.; however, the reaction is most conveniently carried out at temperatures of about 20° to 70° C. Workup of the reaction mixture to isolate the product is carried out in conventional procedures.

The alkanoyl halides employed as starting materials in this reaction route are generally prepared by electrochemical fluorination and therefore often contain isomers. It may be desirable to purify the anilide products to remove straight-chain isomers. It has been found that this can generally be achieved by selective hydrolysis of the straight-chain carboxanilides, and separation of the water soluble K or Na salt of the branched chain carboxanilide from the precipitated aniline. This is illustrated by Examples 28, 29 and 31 below.

The present invention also includes salts of the parent compounds. These salts are prepared in entirely conventional methods. The sodium and potassium salts are prepared by reacting the corresponding parent compounds with sodium or potassium hydroxide; the ammonium salts can be obtained by reacting the parent compound with a compound of the formula

or by reacting a sodium salt of a present compound with

(where X=Br, Cl, or F).

The synthesis of the present compounds is further taught by the following illustrative examples.

EXAMPLE 1

2'-Bromo-4'-nitro-1,2,2,3,3,4,4,5,5,6,6-undecafluorocyclohexanecarboxanilide.

1,2,2,3,3,4,4,5,5,6,6-Undecafluorocyclohexanecarbonyl fluoride estimated to be of 60% purity (10.9 grams; 0.02 mole) and triethylamine (2 grams; 0.02 mole) were placed in 25 ml of diethyl ether. 2-Bromo-4-nitroaniline (11.35 grams; 0.02 mole) in 75 ml of diethyl ether was added dropwise at ambient temperature of about 25° C. The reaction mixture was then stirred for 1½ hours. TLC showed no remaining aniline starting material. The reaction mixture was washed with water three times and with dilute sodium bicarbonate solution once, and thereafter dried. The solvent was then removed by evaporation. The product residue was chromatographed on silica gel HPLC with ethyl acetate:hexane 1:5, which yielded 14.5 grams of product containing occluded solvent. It was recrystallized from hexane and air dried, yielding 5.0 grams (48%) of purified product melting at 98°–101° C. An additional 1 gram was obtained from the mother liquor for a total yield of 57%.

Analysis calculated for $C_{13}H_4BrF_{11}N_2O_3$; Theory C, 29.74; H, 0.77; N, 5.34; Found: C, 30.14; H, 0.91; N, 5.81.

Other compounds of the present invention, prepared in essentially the same procedures, are listed below.

EXAMPLE 2

2'-Iodo-4'-nitro-1,2,2,3,3,4,4,5,5,6,6-undecafluorocyclohexanecarboxanilide, m.p., 125°–127° C., yield 38%.

Analysis calculated for $C_{13}H_4F_{11}IN_2O_3$; Theory: C, 27.35; H, 0.70; N, 4.89; Found: C, 27.11; H, 0.67; N, 4.68.

EXAMPLE 3

2',4'-Dinitro-1,2,2,3,3,4,4,5,5,6,6-undecafluorocyclohexanecarboxanilide, m.p., 106°–109° C., yield 14%.

Analysis calculated for $C_{13}H_4F_{11}N_3O_5$; Theory: C, 31.79; H, 0.82; N, 8.55, F, 42.54; Found: C, 32.77; H, 0.84; N, 9.43, F, 43.66.

EXAMPLE 4

2'-Chloro-5'-nitro-1,2,2,3,3,4,4,5,5,6,6-undecafluorocyclohexanecarboxanilide, m.p., 115°–118° C., yield 24%.

Analysis calculated for $C_{13}H_4ClF_{11}N_2O_3$; Theory: C, 32.53; H, 0.63; N, 5.84; Found: C, 32.50; H, 0.73; N, 5.66; Found: C, 32.22; H, 0.84; N, 5.62.

EXAMPLE 5

2'-Chloro-4'-nitro-1,2,2,3,3,4,4,5,5,6,6-undecafluorocyclohexanecarboxanilide, m.p., 90°–93° C., yield 31%.

Analysis calculated for $C_{13}H_4ClF_{11}N_2O_3$; Theory: C, 32.48; H, 0.83; N, 5.82; Found: C, 33.60; H, 1.01; N, 7.32.

EXAMPLE 6

2'-Cyano-4'-nitro-1,2,2,3,3,4,4,5,5,6,6-undecafluorocyclohexanecarboxanilide, m.p., 119°–120° C., yield 20%.

Analysis calculated for $C_{14}H_4F_{11}N_3O_3$; Theory: C, 35.69; H, 0.86; N, 8.92; Found: C, 35.94; H, 1.13; N, 8.66.

EXAMPLE 7

2'-Cyano-4'-chloro-1,2,2,3,3,4,4,5,5,6,6-undecafluorocyclohexanecarboxanilide, m.p., 122°–124° C.

EXAMPLE 8

2'-(Trifluoromethyl)-4'-bromo-1,2,2,3,3,4,4,5,5,6,6-undecafluorocyclohexanecarboxanilide, m.p., 104°–106° C.

Analysis calculated for $C_{14}H_4BrF_{14}NO$; Theory: C, 30.70; H, 0.73; N, 2.56; Found: C, 31.01; H, 0.69; N, 2.24.

EXAMPLE 9

2',3'-Dichloro-1,2,2,3,3,4,4,5,5,6,6-undecafluorocyclohexanecarboxanilide, m.p., 89°–91° C.

EXAMPLE 10

2'-Methyl-4'-nitro-5'-chloro-1,2,2,3,3,4,4,5,5,6,6-undecafluorocyclohexanecarboxanilide, m.p., 154°–156° C., yield 33%.

Analysis calculated for $C_{14}H_6ClF_{11}N_2O_3$; Theory: C, 33.99; H, 1.22; N, 5.66; Found: C, 34.18; H, 1.41; N, 5.56.

EXAMPLE 11

2',6'-Dichloro-4'-nitro-1,2,2,3,3,4,4,5,5,6,6-undecafluorocyclohexanecarboxanilide, m.p., 155°–157° C.

EXAMPLE 12

2',4',6'-Trichloro-1,2,2,3,3,4,4,5,5,6,6-undecafluorohexanecarboxanilide, m.p., 170°–172° C., yield 39%.

Analysis calculated for $C_{13}H_3Cl_3F_{11}NO$; Theory: C, 30.98; H, 0.60; N, 2.78; Found: C, 30.97; H, 0.52; N, 2.55.

EXAMPLE 13

2'-Nitro-4',6'-dichloro-1,2,2,3,3,4,4,5,5,6,6-undecafluorocyclohexanecarboxanilide, m.p., 97°–99° C.

EXAMPLE 14

2',3',4',5'-Tetrachloro-1,2,2,3,3,4,4,5,5,6,6-undecafluorocyclohexanecarboxanilide, m.p., 130° C., yield 19%.

Analysis calculated for $C_{13}H_2Cl_4F_{11}NO$; Theory: C, 2897; H, 0.37; N, 2.60; Found: C, 29.21; H, 0.60; N, 2.77.

EXAMPLE 15

2',3',4',5',6'-Pentachloro-1,2,2,3,3,4,4,5,5,6,6-undecafluorocyclohexanecarboxanilide, m.p., 181°–184° C., yield 38%.

EXAMPLE 16

N-(5-Nitro-2-pyridyl)-1,2,2,3,3,4,4,5,5,6,6-undecafluorocyclohexanecarboxamide, m.p., 110°–112° C., yield 24%.

Analysis calculated for $C_{12}H_4F_{11}N_3O_3$; Theory: C, 32.29; H, 0.89; N, 9.35; Found: C, 32.16; H, 0.74; N, 9.22; Found: C, 32.27; H, 0.84; N, 9.23.

EXAMPLE 17

2'-Bromo-4'-nitro-1,2,2,3,3,4,4,5,5,6,6-undecafluorocyclohexanecarboxanilide, sodium salt 2'-Bromo-4'-nitro-1,2,2,3,3,4,4,5,5,6,6-undecafluorocyclohexanecarboxanilide (2.6 grams; 0.005 mole) and sodium hydroxide (0.2 gram; 0.005 mole) were combined in 50 ml of acetone at room temperature of about 25° C. All volatiles and water were removed by evaporation. The solid residue was dissolved in hot toluene/ethyl acetate; the product did not crystallize but formed lumps. These were separated and vacuum dried. The yield was 2.1 gram (77%), m.p., 200° C. with decomposition.

Analysis calculated for $C_{13}H_3BrF_{11}N_2O_3Na$; Theory: C, 28.54; H, 0.55; N, 5.12; Found: C, 28.84; H, 1.10; N, 4.90.

EXAMPLE 18

2'-Bromo-4'-nitro-1,2,2,3,3,4,4,5,5,6,6-undecafluorocyclohexanecarboxanilide, tetraethylammonium salt.

2'-Bromo-4'-nitro-1,2,2,3,3,4,4,5,5,6,6-undecafluorocyclohexanecarboxanilide (2.6 grams; 0.005 mole) was dissolved in 25 ml. of acetone and 2N sodium hydroxide (0.2 gram; 0.005 mole) was added all at once. Tetraethylammonium bromide (1.1 gram; 0.005 mole) was then added and the reaction mixture was stirred until it became a single phase. The reaction mixture was poured into ice/water, extracted with methylene chloride/brine, dried over magnesium sulfate, and evaporated. NMR showed a mixture of the intended salt and the parent compound. The residue was therefore dissolved in acetone, retreated with sodium hydroxide and tetraethylammonium bromide, and worked up as before, yielding 1.5 grams (46% yield) of the 2'-bromo-4'-nitro-1,2,2,3,3,4,4,5,5,6,6-undecafluorocyclohexanecarboxanilide, tetraethylammonium salt as an oil.

EXAMPLE 19

2'-Bromo-4'-nitro-1,2,2,3,3,4,4,5,5,6,6-undecafluorocyclohexanecarboxanilide, tetra-n-propylammonium salt.

2'-Bromo-4'-nitro-1,2,2,3,3,4,4,5,5,6,6-undecafluorocyclohexanecarboxanilide (2.6 grams; 0.005 mole) was dissolved in 50 ml. of acetone and 1N sodium hydroxide (5.0 ml., 0.005 mole) was added all at once. Tetrapropylammonium bromide (1.35 gram; 0.005 mole) was then added and the reaction mixture was stirred until it became one phase. The reaction mixture was then poured over ice/water, and an oily solid separated. It was extracted with diethyl ether, dried over magnesium sulfate, evaporated, and crystallized at −10° C. from water/ethanol. 0.9 gram (25% yield) of the tetra-n-propylammonium salt was obtained, m.p., 86°–87° C.

Employing essentially the same procedures as the preceding two examples, the following additional salts were obtained. The identity of the salts was verified by H-NMR.

EXAMPLE 20

2'-Bromo-4'-nitro-1,2,2,3,3,4,4,5,5,6,6-undecafluorocyclohexanecarboxanilide, dimethylbis($C_{14}$–$C_{18}$)-ammonium salt, an oil, yield 39%.

Yet other representative compounds are listed below. Unless indicated otherwise, each was prepared by essentially the same procedures as in Example 1 or in Examples 18–19.

EXAMPLE 21

2'-Chloro-5'-(fluorosulfonyl)-1,2,2,3,3,4,4,5,5,6,6-undecafluorocyclohexanecarboxanilide, m.p., 107°–108° C., yield 30%.

Analysis calculated for $C_{13}H_4ClF_{12}NO_3S$; Theory: C, 30.17; H, 1.14; N, 2.71; Found: C, 30.16; H, 1.01; N, 2.78.

EXAMPLE 22

N-(2-Bromo-4-nitro-1-naphthyl)-1,2,2,3,3,4,4,5,5,6,6-undecafluorocyclohexanecarboxamide, m.p., 152°–154° C., yield 20%.

Analysis calculated for $C_{17}H_6BrF_{11}N_2O_3$; Theory: C, 35.50; H, 1.05; N, 4.87; Found: C, 35.26; H, 1.06; N, 4.76.

EXAMPLE 23

2'-Bromo-4'-nitro-3-(trifluoromethyl)-1,2,2,3,4,4,5,5,6,6-decafluorocyclohexanecarboxanilide.

In a Teflon jar equipped with a stainless steel condensor maintained at from −40° to −50° C., approximately 130 cc of commercial anhydrous HF underwent a pre-electrolysis to remove the last traces of water. An electrode pack of about 2 in$^3$ in size consisting of alternating nickel and carbon steel plates was used under a nitrogen atmosphere at a maximum current density of about 20 ma/cm$^2$ and at or below a cell voltage of 5.2 volts relative to a copper reference electrode 4.2 g (0.02 moles) of distilled m-(trifluoromethyl)benzoyl chloride was added, and 5.6 amp hrs was passed (75% of theoretical). The reaction mixture was extracted with three 20 cc portions of CFCl$_3$, and the extracts were added to 3.2 g of 2-bromo-4-nitro-aniline (0.015 moles) and 2.5 g (0.025 moles) of triethylamine in 25 cc methylene chloride. The organic layer was washed with dilute HCl, dried over sodium sulfate, and chromatographed on silica gel with toluene to give 2'-bromo-4'-nitro-3-(trifluoromethyl)-1,2,2,3,3,4,4,5,5,6,6-decafluorocyclohexanecarboxanilide, m.p., 55°–60° C., yield 35% from acid chloride, (after recrystallization from toluene, m.p., 79°–82° C.). F$^{19}$ NMR was consistent with a mixture of cis/trans isomers. A similar procedure was used in preparing each of Examples 24 and 25.

Analysis calculated for C$_{14}$H$_4$BrF$_{13}$N$_2$O$_3$; Theory: C, 29.24; H, 0.70; N, 4.87; Found: C, 29.20; H, 0.83; N, 5.16; Found after recrystallization: C, 29.14; H, 0.66; N, 4.77.

A 4% yield of the same product, likewise a mixture of cis/trans isomers, was obtained using m-toluoyl chloride in the above reaction, by separating the product acid fluoride from HF without the benefit of extraction. Found: C, 29.36; H, 0.80; N, 4.79.

EXAMPLE 24

2'-Bromo-4'-nitro-4-(trifluoromethoxy)-1,2,2,3,3,4,4,5,5,6,6-decafluorocyclohexanecarboxanilide, m.p., 90°–92° C., yield 20% from p-(trifluoromethoxy)-benzoyl chloride (after recrystallization from toluene, m.p., 101°–104° C.).

Analysis calculated for C$_{14}$H$_4$BrF$_{13}$N$_2$O$_4$; Theory: C, 28.45; H, 0.68; N, 4.74; Found: C, 28.64; H, 0.69; N, 4.47; Found after recrystallization: C, 28.42; H, 0.73; N, 4.64.

EXAMPLE 25

50:50 Mixture of 2'-bromo-4'-nitro-4-chloro-1,2,2,3,3,4,5,5,6,6-decafluorocyclohexanecarboxanilide and 2'-bromo-4'-nitro-1,2,2,3,3,4,4,5,5,6,6-undecafluorocyclohexanecarboxanilide, m.p., 78°–84° C., yield 11% from p-chlorobenzoyl chloride.

Analysis calculated for C$_{13}$H$_4$BrClF$_{10}$N$_2$O$_3$; Theory: C, 28.83; H, 0.74; N, 5.17; Found: C, 29.15; H, 0.93; N, 4.86.

EXAMPLE 26

2',4'-Dinitro-1,2,2,3,3,4,4,5,5,6,6-undecafluorocyclohexanecarboxanilide, dimethylbis(C$_{10}$–C$_{18}$) ammonium salt, an oil, yield 92%.

EXAMPLE 27

2'-Bromo-4'-nitro-2,3,3,3-tetrafluoro-2-(trifluoromethyl)propionanilide (olefin process)

Potassium fluoride (23 grams; 0.4 mole) which was dried by heating strongly with a bunsen burner in a porcelain crucible and subsequently powdered, was added to 200 ml of a DMF solution of 2-bromo-4-nitrophenyl isocyanate (6 grams; 0.025 mole). The mixture was placed in a pressure vessel, purged with a small stream of hexafluoropropene, and heated to 70° C. while adding hexafluoropropene from a pre-weighed supply cylinder at 10–20 psig. A pressure drop occurred as the gas reacted, and the remaining hexafluoropropene was added intermittently until the supply cylinder was empty; heating was continued at 65°–70° C. for 2½ hours with pressure stabilized at 5 psig. The reaction vessel was then cooled and the solution poured off and extracted with hexane.. The DMF solution was poured into water and filtered. The solid products were taken up in chloroform, dried over sodium sulfate, filtered, evaporated, and chromatographed on silica gel with ethyl acetate/hexane (1:5). The front-running product was collected; H-NMR of this product indicated the desired product The material was then chromatographed on silica gel with gradient elution from 100% hexane to 100% ethyl acetate.

The foregoing procedures yielded a waxy solid, m.p. 57°–59° C., yield 1.65 grams (16%). The identity of the product was confirmed by MS, H-NMR, and F$^{19}$-NMR Analysis calculated for C$_{10}$H$_4$BrF$_7$N$_2$O$_3$; Theory: C, 29.08; H, 0.98; N, 6.78; Found: C, 29.31; H, 0.83; N, 6.58.

EXAMPLE 28

2'-Bromo-4'-nitro-2,3,3,3-tetrafluoro-2-(trifluoromethyl)propionanilide (alkanoyl fluoride process, with isomer purification)

2-Bromo-4-nitroaniline (141 grams; 0.65 mole) was dissolved in 3.5 liters of diethyl ether, dried over sodium sulfate, and filtered Triethylamine (71 grams; 0.070 mole) was added with stirring. A mixture of 2,2,3,3,4,4,4-heptafluorobutyryl fluoride, 2,3,3,3-tetrafluoro-2-(trifluoromethyl)propionyl fluoride, HF, and inert gases were employed. The mixture was believed to contain 70% of chemically active acyl fluorides; 100 grams of this mixture were add under a dry ice/acetone condensor. The reaction mixture was left to stand overnight (about 17 hours) and an additional amount of the mixture was added to a total of 210 grams (0.70 mole).

Water was added to the reaction mixture, then dilute ice/HCl until the pH of the aqueous layer was acidic. The water layer was decanted off. The diethyl ether layer was dried over magnesium sulfate and the solvent evaporated under vacuum.

The solid residue was taken up in 800 ml of ethanol, and treated with potassium carbonate at room temperature, with magnetic stirring. Sixty-eight grams of K$_2$CO$_3$ was added initially, followed by 23 g more after 24 hours and 12 g more after 48 hours and stirred for a total of 64 hours. The ethanol was evaporated under vacuum, and the solids were triturated three times with aqueous potassium carbonate. The solution was filtered and the filtrate was acidified below 25° C. with HCl. The product was filtered, washed with water, dissolved in methylene chloride, dried, and evaporated. The gas chromatogram of the product indicated less than 1% straight-chain isomer, m.p., 66° C., yield, 178 grams (66%).

Analysis calculated for C$_{10}$H$_4$BrF$_7$N$_2$O$_3$; Theory: C, 29.08; H, 0.98; N, 6.78; Found: C, 29.30; H, 0.92; N, 6.99.

EXAMPLE 29

2'-Bromo-4'-nitro-2,3,3,3-tetrafluoro-2-(trifluoromethyl)propionanilide (alkanoyl fluoride process, with isomer purification)

2-Bromo-4-nitroaniline (35.84 grams; 0.16 mole), triethylamine (21.15 grams; 0.21 mole), and 250 ml of tetrahydrofuran were added to a 500 ml round-bottom flask equipped with a dry ice/acetone reflux condenser and a gas inlet. The vessel was purged with nitrogen. The same mixture of acyl fluorides used in Example 2 was employed as the reactant in the present example (54.60 grams; 0.18 mole). This mixture was added at a rate allowing a slow reflux. The addition required approximately 90 minutes and the resulting brown solution was stirred for about an hour after the addition was complete.

The reaction mixture was then washed with 60 ml of a 50/50 mixture of water/saturated sodium chloride solution and 40 ml of saturated sodium chloride solution. The aqueous layers were discarded.

One hundred fifty milliliters of 1N sodium hydroxide was then added to the organic layer and 90 ml of volatile material was distilled off at atmospheric pressure. Another 100 ml of 1N sodium hydroxide was added to the solution, and the resulting solution was distilled until the head temperature rose above the boiling point of tetrahydrofuran, 66° C. The pot temperature was held constant until HPLC confirmed the hydrolysis of the straight-chain product by the basic solution. The resulting aniline precipitated out at this time and was removed by filtration.

The filtrate was allowed to cool, then washed twice, with 150 ml and 100 ml of methylene chloride. The aqueous layer was separated and placed under vacuum to remove any residual organic solvents. The solution was then placed in an ice bath and the pH was lowered to 7 with concentrated hydrochloric acid. The desired 2'-bromo-4'-nitro-2,3,3,3-tetrafluoro-2-(trifluoromethyl)-propionanilide precipitated and was separated by filtration, washed with distilled water, and dried overnight in vacuo at room temperature, 42.95 grams (86.0%) in 99.5% purity by HPLC.

Other compounds of the present invention were prepared by the alkanoyl fluoride procedure except where noted otherwise. Preparations by the alkanoyl fluoride process were isolated as isomer mixtures except as noted in Example 31.

These other compounds of the present invention are listed in the following Examples. In each example, the identity of the product was confirmed by H-NMR. The percentage of the desired branched chain isomer in the product, as determined by $F^{19}$-NMR, is also reported.

EXAMPLE 30

2'-(trifluoromethyl)-4'-nitro-2,3,3,3-tetrafluoro-2-(trifluoromethyl)propionanilide, m.p., 53°–54° C. yield 15% (>95% branched isomer).

Analysis calculated for $C_{11}H_4F_{10}N_2O_3$; Theory: C, 32.85; H, 1.00; N, 6.97; Found: C, 32.79; H, 1.15; N, 7.01.

EXAMPLE 31

Preparation #1

2',5'-Dichloro-4'-nitro-2,3,3,3-tetrafluoro-2-(trifluoromethyl)propionanilide was prepared by the olefin procedure, m.p. 80°–82° C., yield 12% (>99% branched isomer).

Analysis calculated for $C_{10}H_3Cl_2F_7N_2O_3$; Theory: C, 29.80; H, 0.75; N, 6.95; Found: C, 29.90; H, 0..53; N, 6.98;

Preparation #2

2',5'-Dichloro-4'-nitro-2,3,3,3-tetrafluoro-2-(trifluoromethyl)propionanilide was also prepared by the alkanoyl fluoride procedure, m.p., 81°–83° C., yield 47% (94% branched isomer). Microanalysis showed
Found: C, 30.07; H, 0.53; N, 6.92.

This product was purified by treatment with potassium carbonate, m.p. 83°–85° C., yield 82% of >99% branched isomer.

EXAMPLE 32

2',6'-Dichloro-4'-nitro-2,3,3,3-tetrafluoro-2-(trifluoromethyl)propionanilide, m.p., 128°–134° C., yield 13% (59% branched isomer).

Analysis calculated for $C_{10}H_3Cl_2F_7N_2O_3$; Theory: C, 29.80; H, 0.75; N, 6.95; Found: C, 29.84; H, 0.97; N, 7.09.

EXAMPLE 33

2'-Methyl-4'-nitro-5'-chloro-2,3,3,3-tetrafluoro-2-(trifluoromethyl)propionanilide, m.p., 114°–116° C., yield 53% (91% branched isomer).

Analysis calculated for $C_{11}H_6ClF_7N_2O_3$; Theory: C, 34.53; H, 1.58; N, 7.32; Found: C, 34.40; H, 1.61; N, 7.31.

EXAMPLE 34

2',4'-Dinitro-2,3,3,3-tetrafluoro-2-(trifluoromethyl)-propionanilide, m.p., 50°–51° C., yield 21% (85% branched isomer).

Analysis calculated for $C_{10}H_4F_7N_3O_5$; Theory: C, 31.68; H, 1.06; N, 11.08; Found: C, 31.42; H, 1.15; N, 10.84.

EXAMPLE 35

2'-Iodo-4'-nitro-2,3,3,3-tetrafluoro-2-(trifluoromethyl)propionanilide, m.p., 107°–110° C., yield 8% (39% branched isomer).

Analysis calculated for $C_{10}H_4IF_7N_2O_3$; Theory: C, 26.11; H, 0.88; N, 6.09; Found: C, 26.28; H, 1.11; N, 5.90.

EXAMPLE 36

2'-Bromo-4'-nitro-2,3,3,3-tetrafluoro-2-(trifluoromethyl)propionanilide, tetra-n-propylammonium salt 2'-Bromo-4'-nitro-2,3,3,3-tetrafluoro-2-(trifluoromethyl)propionanilide, (20 grams of material free of straight-chain isomer; 0.048 mole) was dissolved in 200 ml of acetone. The solution was maintained at room temperature while 2N sodium hydroxide (25 ml; 0.05 mole) and tetra-n-propylammonium bromide (13.5 grams; 0.051 mole) were added. The reaction mixture was stirred for 45 minutes, evaporated at room temperature, and partitioned between methylene chloride/water. The organic phase was washed twice with water, dried over sodium sulfate, and evaporated to dryness, yielding 28.7 grams of the intended salt (99% yield). The identity of the product was confirmed by H-NMR. The product solidified upon standing, m.p., 57°–65° C.

Analysis calculated for $C_{22}H_{31}BrF_7N_3O_3$; Theory: C, 44.16; H, 5.22; N, 7.02; Found: C, 44.14; H, 5.05; N, 6.80.

A second preparation was conducted similarly, and the identity of the product was confirmed by H-NMR. The yield was 9.2 grams (91%), m.p. 72°–75° C.
Found: C, 43.88; H, 4.50; N, 6.83.

A third preparation was similarly conducted, except the starting anilide was only 86% of the desired 2'-bromo-4'-nitro-2,3,3,3-tetrafluoro-2-(trifluoromethyl)-propionanilide, the remaining 14% being the corresponding straight-chain isomer. The product of this reaction was an oil. The identity was confirmed by H-NMR.
Found: C, 44.02; H, 5.07; N, 7.02.

Other salts were prepared in similar manner and are reported below. In each preparation, the identity of the product was confirmed by H-NMR. The starting anilide in these preparations, and therefore the corresponding salt as well, was either essentially pure 2'-bromo-4'-nitro-2,3,3,3-tetrafluoro-2-(trifluoromethyl)propionanilide (referred to as "isomer pure") or a mixture of 86% of this compound and 14% of the corresponding straight-chain isomer (referred to as "86% isomer").

EXAMPLE 37

2'-Bromo-4'-nitro-2,3,3,3-tetrafluoro-2-(trifluoromethyl)propionanilide, dimethylbis($C_{14}$–$C_{18}$)ammonium salt, monohydrate, an oil, yield 45% (86% isomer).

EXAMPLE 38

2'-Bromo-4'-nitro-2,3,3,3-tetrafluoro-2-(pentafluoroethoxy)propionanilide, yield 51%, in mixture with 2'-bromo-4'-nitro-2,2,3,3-tetrafluoro-3-(pentafluoroethoxy)propionanilide and an unidentified third component.

Analysis calculated for $C_{11}H_4BrF_9N_2O_4$; Theory: C, 27.56; H, 0.84; N, 5.85; Found: C, 27.46; H, 0.91; N, 5.75.

EXAMPLE 39

The mixture from the preceding example was purified by treatment with $K_2CO_3$/ethanol, yielding 2'-bromo-4'-nitro-2,3,3,3-tetrafluoro-2-(pentafluoroethoxy)-propionanilide, m.p., 49° C., yield 50% (14% unidentified third component).

Analysis calculated for $C_{11}H_4BrF_9N_2O_4$; Theory: C, 27.58; H, 0.84; N, 5.85; Found: C, 27.80; H, 1.04; N, 6.08.

EXAMPLE 40

2'-Bromo-4'-nitro-2,3,3,3-tetrafluoro-2-(octafluoromorpholino)propionanilide, m.p., 50°–52° C., yield 74% (>99% branched isomer).

Analysis calculated for $C_{13}H_4BrF_{12}N_3O_4$; Theory: C, 27.20; H, 0.70; N, 7.32; Found: C, 27.42; H, 0.75; N, 7.32.

EXAMPLE 41

2'-Bromo-4'-nitro-2,3,3,3-tetrafluoro-2-(heptafluoro-n-propoxy)propionanilide, m.p., 49°–51° C., yield 35%. A minor component of 2'-bromo-4'-nitro-2,3,3,3-tetrafluoro-2-(nonafluoro-n-butoxy)propionanilide was detected by $F^{19}$-NMR.

Analysis calculated for $C_{12}H_4BrF_{11}N_2O_4$; Theory: C, 27.22; H, 0.76; N, 5.29; Found: C, 26.99; H, 0.72; N, 5.55.

Starting Materials

The starting materials used in the above Examples are either known compounds or are prepared in known procedures. Essentially all of the anilines are known compounds. 1-Aminonaphthalene and 2-amino-5-nitropyridine are likewise known compounds. Among the acyl halide starting materials perfluorocyclohexyl with no substituents is known. The remaining perfluorocyclohexyl acyl halides are prepared in known procedures. Typically, a substituted benzoyl halide or benzoic acid is electrochemically fluorinated to the desired starting material. Because this process results in fluorination of all replaceable groups, the necessary benzoyl halide or benzoic acid bears a precursor substituent which is converted to the substituent on the desired starting material. Conversion of such substituent groups in the process of electrochemical fluorination is known.

In addition, most of the starting alkanoyl halides can be prepared by electrochemical fluorination of precursor non-fluorinated compounds.

A general reference on electrochemical fluorination is "Chemistry of Organic Fluorine Compounds" by M. Hudlicky (Horwood Ltd., 1976), especially page 73.

Thus, the compounds which serve as the substituted cyclohexane acyl fluoride starting materials are prepared in known procedures from appropriately substituted benzoyl halides. However, as an exception to the foregoing, those starting acyl fluorides which bear a chlorine substitutent require a chlorine-substituted benzoic acid or acid halide, inasmuch as chlorine survives replacement in the course of electrochemical fluorination.

Electrochemical fluorination results in some rearrangement to isomers which are $CF_3$-substituted, cycloalkyl acyl fluorides in which the cycloalkyl ring contains one less carbon atom than the starting ring. Thus, electrochemical fluorination of a benzoyl halide yields small amounts of $CF_3$-substituted perfluorinated cyclopentanoyl fluorides. Because anilides made from these fluorides share the activity of the present invention, there is no need to remove the rearranged isomers.

The compounds of the present invention exhibit excellent molluscicidal activity. This activity is illustrated by the following tests.

DEROCEROUS ACTIVITY SCREENING TEST

Representative compounds were evaluated against mature grey field slugs, *Derocerus retaculatum* (Muller 1774) also known synonymously as *Agriolimax reticulatus* (Muller), Phylum Mollusca, Class Gastropoda, Family Limacidae. Mature *D. reticulatum* were collected from field infestations and held in polythene boxes containing leaves of various brassica cultivars until required for testing.

Activity tests were carried out in 150 ml plastic cups containing 75 g soil (3% organic matter, sandy clay loam of medium texture).

Compounds for evaluation were dissolved in reagent grade ethanol. Bait pellets were prepared by mixing 45 parts wheat bran with 45 parts molassed sugar beet and 10 parts pre-gelled starch. This mixture was added to the ethanolic solution of test compounds and thoroughly mixed, together with another ten parts of water. For screening purposes the final concentration of test compound in the future bait mixture was 5%. The bait mixture was pelleted by inserting it in glass tubes of 2 mm internal diameter and compressing the mixture with a 2 mm diameter rod. The resultant pellets were oven dried at 50° C., except for compounds of examples 20, 26 and 37 which were dried at 25° C.

Bait pellets for assay were cut into smaller pellets of 20 mg, and one such pellet was placed in each assay pot. One specimen of *D. reticulatum* was placed in each pot and the pot was covered with a lid, perforated to allow ventilation. 1 Day (24 hours) after commencement a 50 mm diameter leaf of Brassica spp. was added for food. A count of live slugs was made 76 hours (3 days) after commencement of a trial. Results were calculated as percentage mortality (corrected for control mortality). For purposes of summary the data from a number of trials have been combined to give an overall rating as follows:

| Mortality Rating | Corrected % Mortality |
| --- | --- |
| 1 | 81–100 |
| 2 | 65–80 |
| 3 | 50–65 |
| 4 | 31–49 |
| 5 | 16–30 |

| Mortality Rating | Corrected % Mortality |
|---|---|
| 6 | 0–15 |

TABLE I

DEROCERUS ACTIVITY SCREENING TEST DATA ACTIVITY OF 5% BAIT PELLETS

| COMPOUND EXAMPLE NO. | MORTALITY RATING AFTER 3 DAYS |
|---|---|
| 1 | 1 |
| 5 | 1 |
| 2 | 1 |
| 11 | 2 |
| 10 | 2 |
| 3 | 3 |
| 6 | 3 |
| 4 | 3 |
| 16 | 4 |
| 8 | 5 |
| 21 | 5 |
| 13 | 5 |
| 22 | 5 |
| 15 | 6 |
| 9 | 6 |
| 14 | 6 |
| 12 | 6 |
| 7 | 6 |
| 20 | 4 |
| 26 | 6 |
| 30 | 1 |
| 31 | 1 |
| 34 | 3 |
| 29 | 4 |
| 35 | 4 |
| 32 | 4 |
| 33 | 5 |
| 37 | 6 |
| 41 | 3 |
| 39 | 3 |
| 24 | 4 |
| 23 | 3 |
| 25 | 3 |
| 40 | 1 |

Further tests were carried out using selected compounds, but using baits having differing quantities of active ingredient. Baits were manufactured as described above, but contained either 0.63%, 1.25%, 2.5% or 5% of active ingredient. Bait pellets of 20 mg weight were used in the Derocerus activity test described above. The results are presented, as percent mortalities, in the following Table II:

ACTIVITY AGAINST SLUGS FORAGING IN ARENAS

Polythene boxes, with a surface area of 0.0625 square meters, were filled to a depth of 50 mm with sterilised soil. Bait pellets containing 5% of the compound of Example 1 were scattered over the soil surface. The number of 20 mg (formulated product) pellets was varied to provide different quantities of active ingredient. Five slugs (*Derocerus reticulatus*) were introduced into each assay box. Slugs were given cabbage as an alternative to the bait pellets from 2 days after treatment. The number of live slugs were counted at 2, 3 and 7 days after treatment. The results are presented in the following Table III:

TABLE III

ACTIVITY OF COMPOUND OF EXAMPLE AGAINST DEROCERUS RETICULATUM IN FORAGING AREAS

| | MG AI/$M^2$ | % Mortality for days after treatment | | |
|---|---|---|---|---|
| | | 2 | 3 | 7 |
| Example 1 | 16 | 93 | 93 | 93 |
| (5% Bait | 32 | 93 | 93 | 93 |
| Pellets) | 64 | 87 | 93 | 93 |
| | 128 | 93 | 100 | 100 |
| Methiocarb | 12.8 | 53 | 93 | 93 |
| (4% Bait | 25.6 | 87 | 100 | 100 |
| Pellets) | 51.2 | 60 | 79 | 93 |
| | 102.4 | 60 | 86 | 100 |
| Control Baits | 0 | 0 | 3 | 10 |

INDIRECT CONTACT ACTIVITY AGAINST THE SLUG, DEROCERUS RETICULATUM

The compound of Example 1 was dissolved in methanol. Replicate 80 mm diameter petri dishes containing a filter paper were sprayed with the methanolic solution of example 1 using a Mardrive Tracked Sprayer fitted with a 8003 flat fan nozzle delivering 40 ml per square meter. After allowing the methanol to evaporate the filter paper was moistened with 1 ml of distilled water and a slug (*D. reticulatum*) was introduced. Counts of live slugs were made at 1 day, when food in the form of brassica leaves was introduced, and at 2 days. The data are presented in the following Table IV:

TABLE II

ACTIVITY OF BAIT PELLETS CONTAINING DIFFERING QUANTITIES OF CARBOXANILIDES AGAINST THE SLUG DEROCERUS RETICULATUM

| | PERCENTAGE OF ACTIVE INGREDIENT IN BAIT PELLET | MG OF ACTIVE INGREDIENT PRESENTED TO SLUG | PERCENT MORTALITY FOR DAYS AFTER TREATENT | |
|---|---|---|---|---|
| | | | 1 | 3 |
| EXAMPLE 1 | 0.63% | 0.125 | 9 | 9 |
| | 1.25% | 0.25 | 27 | 45 |
| | 2.5% | 0.5 | 45 | 100 |
| | 5% | 1 | 64 | 100 |
| EXAMPLE 20 | 2.5% | 0.5 | 64 | 64 |
| | 5% | 1 | 45 | 45 |
| EXAMPLE 29 | 2.5% | 0.5 | 27 | 45 |
| | 5% | 1 | 45 | 64 |
| EXAMPLE 37 | 2.5% | 0.5 | 9 | 27 |
| | 5% | 1 | 0 | 9 |
| CONTROL BAIT PELLET | 0% | | 8% | 8% |

TABLE IV

CONTACT ACTIVITY OF COMPOUND OF EXAMPLE 1
AGAINST DEROCERUS RETICULATUM

| EXAMPLE 1 | % Mortality for Days After Treatment | |
|---|---|---|
| AT PPM AI | 1 DAT | 2 DAT |
| 6.25 | 0 | 0 |
| 12.5 | 0 | 0 |
| 25 | 64 | 100 |
| 50 | 64 | 100 |
| 100 | 100 | 100 |
| 200 | 100 | 100 |
| 0 | 8 | 8 |

Activity of Soil Incorporated Compounds Against
*Derocerus Reticulatum*

The compound of Example 1 was taken up in methanol. The methanolic solution was sprayed onto 500 g sterilised soil in the bowl of a food mixer and incorporated into the soil by mixing for 3 minutes. Compounds of Examples 1, 20, 29 and 37, made up as 10% granules, were added to 500 g of sterilised soil in the bowl of a food mixer and incorporated into the soil by mixing as described above.

75 Gram aliquots of treated soil were added to 150 ml plastic pots and one *Derocerus reticulatum* was introduced into each pot with a 50 mm diameter brassica leaf disc.

Ten days after initiating the experiment the amount of consumption by slugs of the food disc was assessed using the Barrett-Horsfall rating system:

| Rating Score | Percent Food Consumption |
|---|---|
| 0 | 0 |
| 1 | 1–3 |
| 2 | 3–6 |
| 3 | 6–12 |
| 4 | 12–25 |
| 5 | 25–50 |
| 6 | 50–75 |
| 7 | 75–88 |
| 8 | 88–94 |
| 9 | 95–97 |
| 10 | 97–99 |
| 11 | 100 |

The food consumption rating scores were translated to mean percent food consumption and percent reduction in feeding by standard computational techniques. The results are presented in the following Table V:

TABLE V

Activity of Soil Incorporated Compounds Against
Derocerus Reticulatum as Measured by Reduction
In Food Consumption

| | | % Reduction in Feeding for mg active ingredient/kg soil | | | | |
|---|---|---|---|---|---|---|
| | | 0.5 | 1 | 2 | 4 | 8 |
| Example 1 | Technical | 70 | 86 | 91 | 93 | 91 |
| Example 1 | 10% Granule | 91 | 97 | 96 | 94 | 91 |
| Example 20 | " | 58 | 88 | 90 | 76 | 91 |
| Example 29 | " | 70 | 76 | 3 | 73 | 46 |
| Example 37 | " | 98 | 97 | 90 | 53 | 93 |

UNTREATED (% FOOD CONSUMPTION) 90%

Molluscs against which the present method can be practised include the species identified above as well as many others, including the following:

ARIONIDAE
  *Arion ater* (Linne)
  *Arion lusitanicus* (Mabille)
  *Arion subfuscus* (Draparnaud)
  *Arion fusciatus* (Nilsson)
  *Arion circumscriptus* (Johnston)
  *Arion hortersis* (Ferussac)
MILACIDAE
  *Milax gagates* (Draparnaud)
  *Milax sowerbyi* (Ferussac)
  *Milax budapesteusis* (Hazay)
LIMACIDAE
  *Limax valentinanis* (Ferussac)
  *Limax nyctaluis* (Bourguignat)
  *Derocerus Caruanae* (Pollonera)
  *Derocerus reticulatum* (Muller)
SUBULINIDAE
  *Subulina striatella* (Rang)
HELICIDAE
  *Cepaea sylvatica* (Drapamaud)
  *Helix aspersa* (Muller)
  *Theba pisana*

Crop Selectivity of 5% Bait Pellets

Bait pellets containing 5% of the compound of Example 1 were tested for crop safety against emerging wheat seedlings. Wooden containers of dimensions 1.5×2.5×0.22 m deep, were filled to a depth of 0.2 m with sterilised soil. Furrows (30 mm deep × 1.5 m) were made into the soil and wheat seed (cv. Broom) were shown into the furrows. The furrows were covered and the soil watered as required. Each wooden container was marked out into six 0.5 meter square plots. One day after emergence of the crop bait pellets were applied by hand to each plot and the plots rated for crop injury and vigour 3, 7 and 14 days after treatment. Results were as set forth in the following Table VI.

TABLE VI

Crop Safety of Molluscicide Bait Pellets
Against Wheat of cv. Broom

| | Rate (MG AI/ Meter$^2$) | % Crop Injury for Days After Treatment | | |
|---|---|---|---|---|
| | | 3 | 7 | 14 |
| Example 1 | 25 | 0 | 0 | 2 |
| | 50 | 2 | 2 | 2 |
| | 75 | 3 | 2 | 2 |
| Methiocarb | 20 | 0 | 0 | 2 |
| Untreated | 0 | 0 | 0 | 2 |

| | | % Crop Vigour for Days After Treatment | | |
|---|---|---|---|---|
| | | 3 | 7 | 14 |
| Example 1 | 25 | 99 | 98 | 98 |
| | 50 | 98 | 98 | 98 |
| | 75 | 97 | 97 | 98 |
| Methiocarb | 20 | 98 | 97 | 98 |
| Untreated | 0 | 98 | 98 | 96 |

Each treatment was replicated 3 times

A similar protocol was followed, but using oil seed rape (*Brassica napus*) cv. Midando, as test crop. The plots were rated for injury and vigour after 10 days. Results were as set forth in Table VII.

TABLE VII

Crop Safety of Molluscicide Bait Pellets
Against Oilseed Rape of cv. Mikando

| | Rate (MG AI M$^2$) | % Crop Injury for 10 Days After Treatment |
|---|---|---|
| Example 1 | 25 | 0 |
| (5% Bait | 50 | 0 |

TABLE VII-continued

Crop Safety of Molluscicide Bait Pellets
Against Oilseed Rape of cv. Mikando

| Pellet) | 75 | 0 |
|---|---|---|
| Methiocarb (4% Bait Pellet) | 20 | 0 |
| | 0 | 0 |

| | | % Crop Stand at 10 Days After Treatment |
|---|---|---|
| Example 1 (5% Bait Pellet) | 25 | 91 |
| | 50 | 95 |
| | 75 | 98 |
| Methiocarb | 20 | 97 |
| UNTREATED | 0 | 96 |

Activity Against An Aquatic Mollusc

Compounds were dissolved in an 1:1 acetone: ethanol mixture containing 10% Toximal 5. The solution was added to distilled water at the rate of 1 ml per 1000 ml. The solution of aqueous material was poured into 250 ml beakers; 100 ml was added to each beaker. Five freshwater rumshom snails, *Planorbis planorbis* (Mollusca, Gastropoda, Family Pulmonata) were added to each beaker. The beakers were covered with parafilm, punctured to allow ventilation, and left for 24 hours at 15° C. when a count of live snails was made.

The results are presented in Table VIII.

TABLE VIII

Activity of Compounds Against the
Aquatic Mollusc, Planorbis Planorbis

| | PPM AI | % Mortality 24 hours After Treatment |
|---|---|---|
| Example 1 | 10 | 100 |
| | 1 | 100 |
| | 0.1 | 41 |
| | 0.01 | 26 |
| | 0.001 | 26 |
| Example 2 | 1 | 100 |
| | 0.1 | 100 |
| Example 3 | 1 | 100 |
| | 0.1 | 82 |
| Example 20 | 1 | 100 |
| | 0.1 | 45 |
| Example 29 | 1 | 100 |
| | 0.1 | 0 |
| Example 37 | 1 | 81 |
| | 0.1 | 11 |

The foregoing illustrates that compounds of the present invention, as well as being applicable against terrestrial molluscs, have possible application against aquatic molluscs. Therefore the invention may also be used in a method of inactivating aquatic molluscs by applying to a locus of the mollusc an effective amount of one or more of the compounds of the present invention. The compounds would be applied using formulations conventionally employed in aquatic situations such as paints, gels, slow release polymers and the like, as well as by employing the compound directly into the aquatic environment. Molluscs, dwelling in aquatic situations, such as rivers, ponds, lakes, flooded meadows and places of aquaculture, include many species among which are found the intermediate hosts of various parasitic diseases of man and his domesticated animals. Such hosts include *Lymnaea truncatula*, one of the intermediate hosts of *Fasciolia hepatica* (the liver fluke), and the many species of pulmonate snails which act as intermediates for blood flukes such as *Schistosoma mansoni*, the causative agents of bilharzia or schistosomiasis.

The present compounds may be employed for the control of molluscs in accordance with standard practices in the agricultural chemical industry. Thus, the compounds, while they can be employed alone, are preferably formulated with conventional additives as described in more detail in the following section. The amount of the present compounds necessary to provide molluscicidal activity is not critical and will vary widely depending on the susceptibility of the particular mollusc species to the compound chosen, weather and the like. In general, when employing the compounds in bait formulations, concentrations in the bait of 1.25% or more are efficacious.

The formulations preferably comprise suitable bait materials, fillers and waterproofing agents. Such a bait formulation may contain from about 0.1 to about 90% by weight of the active ingredient.

Bait formulations are typically based on food materials, e.g. wheat, soya bran, corn bran and other similar materials, either singly or in combinations. The food materials may be mixed with fillers such as limestone and/or binders such as lignin sulphonate or pre-gelled starch, and/or water repellents and/or waterproofing agents such as gelatin, Silicone oil and silica. Bait formulations are typically formulated as pellets, for both application to the soil surface or into the soil with seeds at drilling.

Other suitable formulations include sprayable formulations, such as wettable powders, aqueous suspensions and emulsifiable concentrates, and solid compositions, such as dusts, granules and flowable pellets.

Sprayable formulations are in the form of concentrated compositions which can be diluted with water to form water dispersions or emulsions containing in the range from about 0.05 to about 10 percent of the active ingredient by weight. Such diluted formulations are sprayed onto molluscs, their locations or their food sources. The concentrated compositions may be either solids, usually referred to as wettable powders or dry flowables, or liquids, usually known as emulsifiable concentrations and aqueous suspension.

A typical wettable powder comprises an intimate mixture of an active ingredient of the invention, an inert carrier, and surfactants. The concentration of the active agent is usually from about 2.5 percent to about 90 percent by weight. The inert carrier is usually chosen from among the attapulgite clays, the montmorillonite clays, the diatomaceous earths, the kaolinites, and the purified silicates. Effective surfactants, comprising from about 0.5 percent to about 10 percent by weight of the wettable powder, are chosen from among the condensed naphthalensulfonates, the alkyl sulphates and the alkyl arylethoxylates, the alkyl sulphates and the alkyl arylethoxylates. Suspending agents, such as the sulphonated lignins can also be added.

A typical emulsifiable concentrate comprises from about 10–750 grams of a compound of the invention per liter of liquid, dissolved in a mixture of organic solvents and emulsifiers. The organic solvent is chosen with regard to its solvency and its cost. Useful solvents include the aromatics, especially the xylenes and the heavy aromatic naphthas. Hydrophilic cosolvents such as DMF, cyclohexanone, and the glycol ethers such as 2-methoxyethanol may be included. Other organic solvents may also be used, including the terpenic solvents and kerosene; methyl heptyl ketone and other high molecular weight esters are also useful. Suitable emulsifiers for emulsifiable concentrates are chosen from the alkylbenzenesulphonates, naphthalenesulphonates, and nonionic surfactants such as alkylphenol adducts of polyoxyethylene, and are used at similar percentages as for wettable powders.

An aqueous suspension, or liquid flowable, is comprised of a finely ground suspension of the active ingredient dispersed in a water based system. This type of formulation is particularly useful for compounds with low water solubility. The concentration of active agent is usually from about 1 to 60 percent by weight. A typical aqueous suspension may comprise wetting and dispersing agents, antifreeze components, thickening or bulking agents, as well as water and the active ingredient.

Dust compositions containing a compound of the present invention usually contain from about 0.1 to about 50 percent by weight of the compound. Dusts are prepared by intimately mixing and finely grinding the active agent with an inert solid such as ground montmorillonite clay, attapulgite clay, talc, ground volcanic rock, kaolin clay, or other inert, relatively dense, inexpensive substances.

Solid, granular compositions are convenient for the application of compounds of this invention to the soil and will contain the active agent in an amount from about 0.1 to about 20 percent by weight. Granules comprise a compound of the invention dispersed on a granular inert carrier such as coarsely ground clay of from about 0.1 to about 3 mm particle size. The active ingredient is most conveniently applied to the clay be dissolving it in an inexpensive solvent, such as acetone, methylene chloride, xylene or other petroleum solvents, methoxy propylene glycol, or the like, and applying the solution to the sized clay in an appropriate solids mixer. The solvent is then typically removed by evaporation; however removal is not essential. Alternatively, any of the present compounds which is an oil can be sprayed, with or without heating, directly onto clay. Likewise, any of the present compounds which is a solid can be melted and then sprayed directly onto clay.

The following Examples give details of representative formulations of the compounds to be employed in accordance with the present invention.

BAIT PELLETS

Baits were prepared by dissolving the compound of Example 1 in ethanol. To this ethanolic solution were added the bait ingredients and 1% w/w water. The ingredients were mixed together and formed into bait pellets by compression in a glass tube with a brass rod. The bait pellet thus formed was placed in an oven for three hours at 50° C. to drive off ethanol and water. cl EXAMPLE A 1.25% Bait Pellet

| Ingredient | Percent by Weight |
| --- | --- |
| Compound of Example 1 | 1.25% |
| Wheat Bran | 44.44% |
| Molassed Sugar Beet | 44.44% |
| Pregelled Starch | 9.87% |

EXAMPLE B 2.5% Bait Pellet

| Ingredient | Percent by Weight |
| --- | --- |
| Compound of Example 1 | 2.5% |
| Wheat Bran | 43.88% |
| Molassed Sugar Beet | 43.88% |
| Pregelled Starch | 9.74% |

EXAMPLE C

5% Bait Pellet

| Ingredient | Percent by Weight |
| --- | --- |
| Compound of Example 1 | 5% |
| Wheat Bran | 42.75% |
| Molassed Sugar Beet | 42.75% |
| Pregelled Starch | 9.5% |

EXAMPLE D

10% Bait Pellet

| Ingredient | Percent by Weight |
| --- | --- |
| Compound of Example 1 | 10% |
| Wheat Bran | 40.5% |
| Molassed Sugar Beet | 40.5% |
| Pregelled Starch | 9% |

The percentage of active ingredient in the bait can be decreased below 1.25% or increased above 10% by varying the percentage of wheat, molassed sugar beet and pregelled starch in the bait pellet.

Baits containing different proportions of bran and molassed sugar beet, as well as other binders, attractants and/or waterproofers can be prepared in a similar manner. For example, a bait which is more waterproof than the above mentioned baits (Examples A-D) can be prepared from the following ingredients:

EXAMPLE E 2 5% Waterproof Bait Pellet

| Ingredient | Percent by Weight |
| --- | --- |
| Compound of Example 1 | 2.5% |
| Wheat Bran | 29.25% |
| Molassed Sugar Beet | 48.74% |
| Lignin Sulphonate | 9.75% |
| Limestone | 4.88% |
| Gelatin | 4.88% |

Only 2.93% of the gelatin was mixed with the other ingredients during the manufacture of the bait pellets; the other 1.95% was sprayed onto the bait pellets after pellet formation.

EXAMPLE F

Emulsifiable Concentrate

A 1 lb/gallon emulsifiable concentrate was prepared by dissolving the compound of Example 1, estimated to be of 97% purity, in xylene and adding Toximul H and Toximul D (each of Toximul H and Toximul D is a sulphonate-nonionic blend of emulsifiers by Stepan Chemical Co.)

| Ingredient | Percent by Weight |
| --- | --- |
| Compound of Example 1 | 13.2 |
| Xylene | 81.8 |
| Toximul H | 3.0 |
| Toximul D | 2.0 |

EXAMPLE G

Wettable Powder

A 20% wettable powder of the compound of Example 1 was prepared by mixing the first five listed ingredients in conventional fashion. After these ingredients had been admixed, 3% of Selogen HR (a dispersing agent produced by Diamond Shamrock) and 3% of a mixture of
(1) 22% of TMN-6, a surfactant sold by Union Carbide, trimethylnonane/6 moles of ethylene oxide,
(2) 28% of Triton x-100, a surfactant sold by Rohm & Hass, ocitylphenol/10 moles of ethylene oxide, and
(3) 50% of HiSil, a lightweight silica sold by Pittsburg Plate Glass Co. were added and blended until uniform. The ingredients and the % of each in the final formulation were as follows:

| Ingredient | Percent by Weight |
| --- | --- |
| Compound of Example 1, 95% purity | 21.06 |
| Stepan ME, sodium lauryl sulphate from Stepan Chemical Co. | 4.72 |
| Polyfon O, a dispersant from Westvaco Corp., Polychemicals Dept. | 4.72 |
| Zeollex-7, a sodium silicoaluminate from J. H. Huber Corp. | 4.72 |
| Barden's clay, a kaolinite | 58.78 |
| Selogen HR | 3.00 |
| Mixture of TMN-6, Triton X-100, and HiSil | 3.00 |

EXAMPLES H–K

1%–10% Granules

A series of four granular formulations of the compound of Example 1 was prepared. In each instance, the appropriate amount of the compound was dissolved in acetone, at the rate of 1 gram of compound per 2 grams of acetone, and the resulting solution was sprayed onto clay under agitation. Thereafter, the acetone was evaporated to provide the final formulation. The clay employed in this series of granular formulations was 30/60 mesh Flores RMV (RMV=regular volatile material), an attapulgite clay produced by the Floridin Co. The compound of Example 1 was estimated to be of 97% purity. The specific granular formulations so produced, each in 50-gram quantity, were as follows.

EXAMPLE H

1% Granule

| Ingredient | Percent by weight |
| --- | --- |
| Compound of Example 1 | 1.03 |
| Clay | 98.97 |

EXAMPLE I

2.5% Granule

| Ingredient | Percent by weight |
| --- | --- |
| Compound of Example 1 | 2.58 |
| Clay | 97.42 |

EXAMPLE J

5.0% Granule

| Ingredient | Percent by weight |
| --- | --- |
| Compound of Example 1 | 5.15 |
| Clay | 94.85 |

| Ingredient | Percent by weight |
| --- | --- |
| Compound of Example 1 | 10.31 |
| Clay | 89.69 |

What is claimed is:

1. A method of controlling molluscs which comprises applying to the infected locus of the molluscs a molluscicidally effective amount of a compound of the formula

wherein $R^1$ represents perfluorocyclohexyl, a perfluorocyclohexyl group of formula $-C_6F_{10}R^2$, a group iso-$C_3F_7$, or a group $-CF(CF_3)R^3$, wherein $R^2$ represents chloro, $-CF_3$ or $-OCF_3$ and $R^3$ represents $-OC_2F_5$ or $-OC_3H_7$; $R^4$ represents a substituted aryl group of the formula

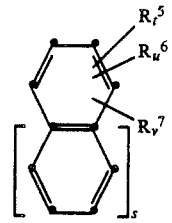

wherein each $R^5$ independently represents bromo or chloro;
  each $R^6$ independently represents iodo, nitro, cyano, $CF_3$ or fluorosulfonyl;
  $R^7$ represents methyl;
  t represents 0–5;
  u represents 0–2;
  v represents 0, or, when at least one $R^5$ or nitro group is present, 1;
  s represents 0 to 1;
  and the sum of t, u and v is 2–5 when each of u, v and s is 0 or 2–3 when any of u, v and s is at least one;
or a sodium, potassium or ammonium salt of the foregoing compound, wherein ammonium is of the following formula

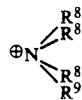

wherein each $R^8$ independently represents alkyl of $C_1$–$C_{20}$, benzyl, 2-hydroxyethyl, 2-hydroxypropyl, or 3-hydroxypropyl; and $R^9$ represents hydrogen or $R^8$, the total number of carbon atoms in all $R^8$ and $R^9$ moieties being from 12 to 60, except that when one or more $R^8$ groups are 2-hydroxyethyl, 2-hydroxypropyl, or 3-hydroxypropyl, the total number of carbon atoms in all $R^8$ and $R^9$ moieties can be from 6 to 60.

2. A method of claim 1 wherein u is 2, t is 0, v is 0 and one of the $R^6$ groups is nitro and the other is iodo or $CF_3$ or t is 1, u is 1, $R^5$ is bromo or chloro and $R^6$ is nitro.

3. A method of claim 1 in which the compound of formula I is
2'-Bromo-4'-nitro-1,2,2,3,3,4,4,5,5,6,6-undecafluorocyclohexanecarboxanilide,
2'-Chloro-4'-nitro-1,2,2,3,3,4,4,5,5,6,6-undecafluorocyclohexanecarboxanilide,
2'-Iodo-4'-nitro-1,2,2,3,3,4,4,5,5,6,6-undecfluorocyclohexanecarboxanilide,
2'-(trifluoromethyl)-4'-nitro-2,3,3,3-tetra-fluoro-2-(trifluoromethyl)propionanilide, or
2',5'-Dichloro-4'-nitro-2,3,3,3-tetrafluoro-2-(trifluoromethyl)propionanilide, or a sodium, potassium, or ammonium salt thereof as defined in claim 1.

4. A method of claim 1 in which the compound of formula I is 2'-bromo-4'-nitro-1,2,2,3,3,4,4,5,5,6,6-undecafluorocyclohexanecarboxanilide or a sodium, potassium, or ammonium salt thereof as defined in claim 1.

5. A method of claim 1 wherein the compound of formula (I) is applied at a rate of from 375 to 500 gm/ha.

* * * * *